United States Patent
Sammak et al.

(10) Patent No.: US 6,917,884 B2
(45) Date of Patent: Jul. 12, 2005

(54) AUTOMATED ASSAY FOR IDENTIFICATION OF INDIVIDUAL CELLS DURING KINETIC ASSAYS

(76) Inventors: Paul Sammak, 551 Olive St., Pittsburgh, PA (US) 15237; Gustavo Rosania, 1805 Vinan Kay Cir., Ann Arbor, MI (US) 48103; Richard Rubin, 216 Gladstone Rd., Pittsburgh, PA (US) 15217; Michel Nederlof, 1502 Fox Chapel Rd., Pittsburgh, PA (US) 15238; Oleg P. Lapets, 1937 Shady Oak Cir., Allison Park, PA (US) 15101; Randall O. Shopoff, 113 Country Club Dr., Pittsburgh, PA (US) 15235; Murugan Kannan, 8988 Meadow Oaks Dr., Allison Park, PA (US) 15101

( * ) Notice: Subject to any disclaimer, the term of this patent is extended or adjusted under 35 U.S.C. 154(b) by 362 days.

(21) Appl. No.: 10/037,285

(22) Filed: Dec. 21, 2001

(65) Prior Publication Data

US 2003/0036853 A1 Feb. 20, 2003

Related U.S. Application Data

(60) Provisional application No. 60/258,147, filed on Dec. 22, 2000.

(51) Int. Cl.$^7$ .............................. G06T 7/00; G06K 9/78; G06K 9/46
(52) U.S. Cl. .......................... 702/21; 382/133; 345/626
(58) Field of Search .......................... 702/21; 382/133; 345/626

(56) References Cited

U.S. PATENT DOCUMENTS

| 5,973,732 A | 10/1999 | Guthrie | 318/169 |
| 5,989,835 A | 11/1999 | Dunlay et al. | 435/7.2 |
| 6,103,479 A | 8/2000 | Taylor | 435/7.2 |

FOREIGN PATENT DOCUMENTS

| WO | WO 98/38490 | 9/1998 |
| WO | WO 00/72258 | 11/2000 |
| WO | WO 01/11340 | 2/2001 |
| WO | WO 01/11341 | 2/2001 |
| WO | WO 01/35072 | 5/2001 |
| WO | WO 01/42786 | 6/2001 |

OTHER PUBLICATIONS

Vollmer et al. Tumor necrosis factor–alpha decreases neutrophil chemotaxis to N-formyl-1-methionyl-1-leucyl-1-phenylalanine: analysis of single cell movement. J. Leukocyte Biology. Dec. 1992. vol. 52, no. 6, pp. 630–636.*
Giuliano, et al., "High–Content Screening: A New Approach to Easing Key Bottlenecks in the Drig Discovery Process", Journal of Biomolecular Screening, Larchmont, Ny, Us, vol. : 4(2), (1997), pp. 249–259.
McNally, J.G., et al., "Computational Optical–Sectioning Microscopy for 3–D Quantification of Cell Motion: Results and Chanllenges", SPIE Jul. 25–26, (1994), vol. : 2302, pp. 342–351.
Han, et al., (2001), Nature Biotechnology, 19:631–635.
Kao, et al., (1989), J. Biol. Chem., 264(14):8179–81843.
Minta, et al., (1989), J. Biol. Chem., 264(14):8171–8178.
Rosenthal, (2001), Nature Biotechnology, 19:621–622.
Soll, (1995), International Review of Cytology, 163:43–104.
Soll, (1988), Cell Motility and the Cytoskeleton, 10:91–106.
Soll, et al., (2001) Method in Molecular Biology, 161:45–58.
Walmond, et al., (2001) Method in Molecular Biology, 161:59–83.

* cited by examiner

Primary Examiner—Marjorie Moran
(74) Attorney, Agent, or Firm—McDonnell Boehnen Hulbert & Berghoff

(57) ABSTRACT

The present invention provides methods and software for tracking individual cells during a kinetic cell screening assay.

21 Claims, 1 Drawing Sheet

AUTOMATED ASSAY FOR IDENTIFICATION OF INDIVIDUAL CELLS DURING KINETIC ASSAYS

CROSS REFERENCE

This application claims the benefit of U.S. Provisional Application for patent Ser. No. 60/258,147 filed Dec. 22, 2000.

FIELD OF THE INVENTION

The application relates to kinetic cell-based screening.

BACKGROUND OF THE INVENTION

Kinetic assays are performed by making measurements at a series of points in time to measure the change of a sample. The measurements at any one time point might also be used for a non-kinetic assay, here called a fixed endpoint assay. Fixed endpoint assays are sufficient for samples that exhibit little or no change over the duration of the assay. If the sample changes over time, kinetic measurements are required to measure those changes. Mathematical descriptions of the trends in various cell parameters over time represent kinetic features that are distinct from the measurements calculated in fixed endpoint assays.

Kinetic assays are performed on the same sample over time and are distinct from common experiments that provide an approximation of kinetic features with fixed endpoint assays on different portions of a sample. For example, if the sample is a population of cells comprising a number of similar individual cells, changes in the population over time can be measured by assaying portions of the sample with a series of fixed endpoint assays. This approach is commonly used in biochemical or immunohistochemical assays when samples are killed (i.e., fixed) or destroyed during the assay. A series of fixed endpoint assays makes measurements on individual cells, but the particular individuals within each population are different at each fixed endpoint assay and cannot be related to each other on the cell level. A series of fixed endpoint assays provides useful kinetic information only when the population average measurements are assumed to be related from portion to portion of the sample and the individual cells in the population are assumed to be equivalent.

The fixed endpoint approach is insufficient if the cells in the sample are not equivalent or if the changes must be related over time on a cell-by-cell basis. Measurements of physiologically relevant cells are heterogeneous, reflecting the normal variability of cell behavior in an intact animal. The heterogeneity often includes important information on the physiology of cells in the living state, and biologically relevant measurements must include, not exclude the variability of the sample. Living cells that change independently of each other must be measured at multiple times and the measurements correlated over time on a cell-by-cell basis.

A true kinetic assay addresses problems by providing measurements on single cells correlated through time. Generally, cells are identified by position and by other characteristics to provide continuity of cell level biological measurement at each time. A typical problem to be overcome is positional uncertainty of cells due to movement of cells or the measuring instrument. The ability to identify cells over time allows the user to measure and account for sample variability, and subpopulation behavior. The whole population response of a sample is often due to the activity of just a subpopulation of cells. Accurate kinetic measurement of subpopulations provides higher content information about physiological, or pharmacological response of a biological sample. Cell-based kinetic measurements also allow multiple measurements of the same sample (multiparametric assays) to be correlated on the cell level, connecting measurements of different cellular functions and mechanisms, and thus providing a better mechanistic understanding of cells and drugs that affect them.

Therefore, methods for tracking individual cells during a kinetic cell screening assay are needed in the art.

SUMMARY OF THE INVENTION

The present invention provides methods and software for tracking individual cells during a kinetic cell screening assay, comprising:

a) providing cells that possess at least a first luminescently labeled reporter molecule that reports on a cell structure;

b) obtaining a structure image from luminescent signals from the at least first luminescently labeled reporter molecule in the cells in a field of view;

c) creating a structure mask for individual cells in the field of view;

d) defining a reference point of each structure mask;

e) assigning an cell identification to each reference point in the field of view;

f) repeating steps (b) through (e) at a second time point;

g) correlating cell identification between the first time point and the second time point by calculating a distance between reference points in the field of view at the first time point and reference points in the field of view at the second time point; and h) defining a cell identification match by identifying reference points in the field of view at the first time point and reference points in the field of view at the second time point that are closest together.

In a preferred embodiment, steps (f)–(h) are repeated a desired number of time points, wherein determining the distance between reference points is done by determining a distance between reference points in successive time points, and wherein defining the closest cell identification match is done by defining the closest cell identification match in successive time points.

In another preferred embodiments include assigning a quality score to the cell identification match based on a distance determined for a second closest cell identification match, wherein a cell identification match is rejected if the quality score is below a user-defined threshold for a quality score.

A further preferred embodiment comprises comparing other features of the individual cells between successive time points in order to facilitate cell identification.

DETAILED DESCRIPTION OF THE PREFERRED EMBODIMENTS

Figure 1:
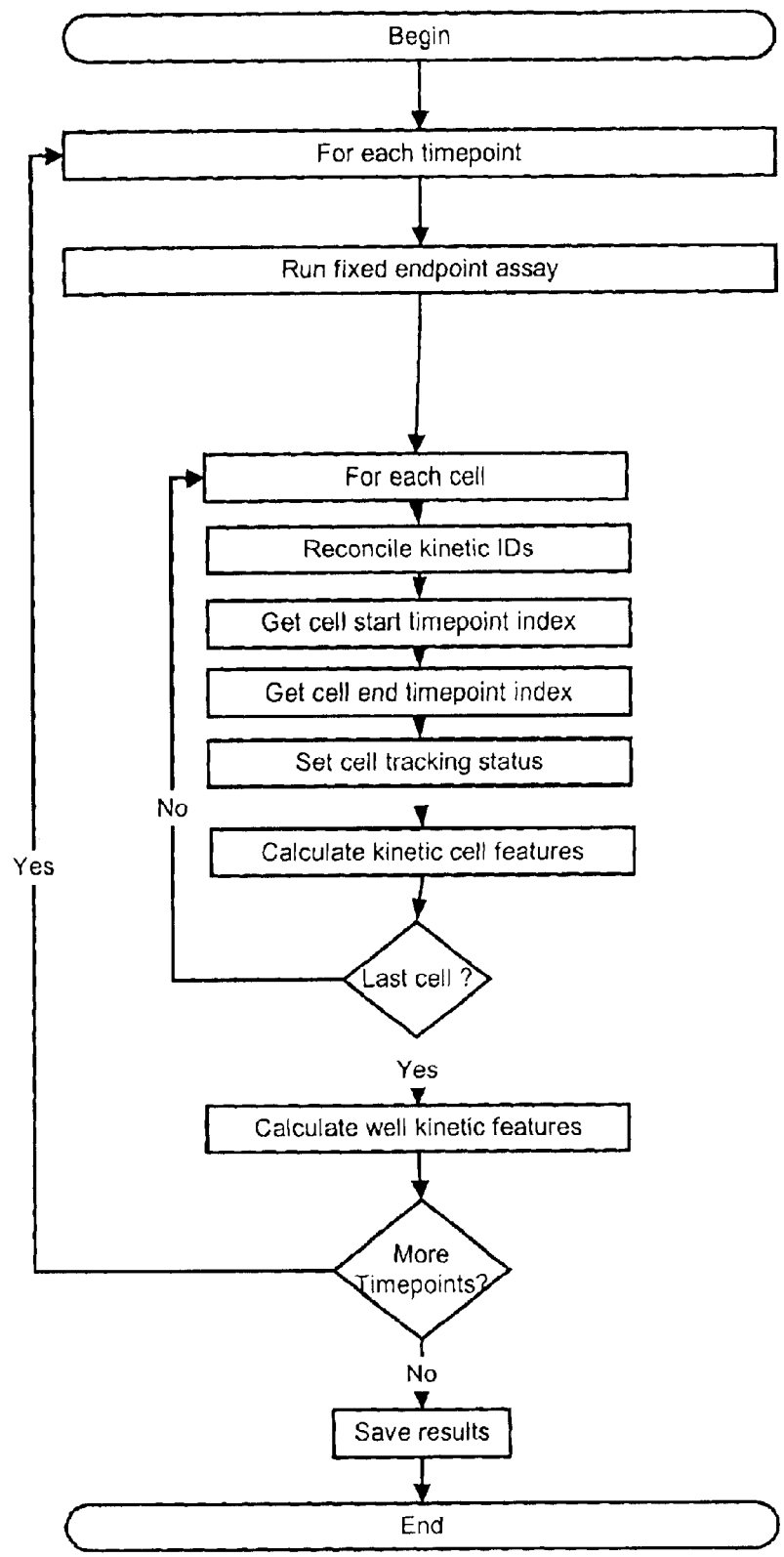
FIG. 1 is a flow chart showing one embodiment of the method for tracking individual cells during a kinetic cell screening assay.

In kinetic assays, cells may move around, enter or leave the field, grow, shrink, or divide; also, separate cells may move into or out of contact with each other. In determining features for individual cells over time, it is preferable to optimize correct identification of individual cells from timepoint to timepoint. Thus, after collecting the data for a current timepoint, a second cell identification is reconciled against a cell identification obtained from the first timepoint in the kinetic scan for the well. This will ensure that the kinetic data is associated with the correct cell throughout all timepoints of the kinetic scan. After obtaining the cell, field, well, and plate level data for the current timepoint, the kinetic data is integrated with any previous kinetic data to form the kinetic features for individual cells, from which field-based, well-based, and/or plate-based kinetic features pertaining to any desired cell screening assay can be derived.

Methods for reconciling cell identification across different time points help insure that any given cell has the same identification from image to image in the image series.

The present invention provides methods and software for tracking individual cells during a kinetic cell screening assay, comprising:

a) providing cells that possess at least a first luminescently labeled reporter molecule that reports on a cell structure;

b) obtaining a structure image from luminescent signals from the at least first luminescently labeled reporter molecule in the cells in a field of view;

c) creating a structure mask for individual cells in the field of view;

d) defining a reference point of each structure mask;

e) assigning an cell identification to each reference point in the field of view;

f) repeating steps (b) through (e) at a second time point;

g) correlating cell identification between the first time point and the second time point by calculating a distance between reference points in the field of view at the first time point and reference points in the field of view at the second time point; and h) defining a cell identification match by identifying reference points in the field of view at the first time point and reference points in the field of view at the second time point that are closest together.

As used herein, the term "image" means a digital representation of the optically detectable signals from the at least first optically detectable reporter molecule, and does not require a specific arrangement or display of the digital representation. Images are parcels of information derived from the sample that are organized in various ways for the convenience of the observer. In preferred embodiments, well known formats for such "images" are employed, including but not limited to DIB, TIFF, BMP, picture element (pixel) maps, three-dimensional volume arrays, two dimensional surface or cross section arrays, or one dimensional line scan images, oscilloscope time traces, orthogonal arrays of integers, pixel intensity numbers, hexagonal grids of integers, floating point pixels, and planar, chunky or Bayer pattern arrays of multispectral pixel arrays. In a most preferred embodiment, picture element (pixel) map images are used, such as those produced by optical cameras where spatial location in one plane (X, Y) within the sample is represented by spatial location within the map (x, y) and luminescent sample intensity (I) is represented by the signal amplitude or value (i) at each pixel.

The Field Of View (FOV) is the area that is imaged. It is equivalent to the image size. The dimension of the FOV can either be expressed in microns at the scale of the sample area, or in pixels of the image size. The cell sample area is generally much larger than the FOV, such as for a medium or high resolution image of a 96, or 384 well plate.

As used herein an "optically detectable reporter molecule" is a reporter molecule that can emit, reflect, or absorb light, and includes, but is not limited to, fluorescent, luminescent, and chemiluminescent reporter molecules. In a preferred embodiment, a fluorescent reporter molecule is used.

The cell structure reported on by the optically detectable reporter molecule can be any detectable cell structure, including nuclei, intracellular organelles, cytosol markers, and plasma membrane markers. In the simplest case, the cell structure is present as a single entity in the cell, such as the nucleus.

As used herein, the reporter molecule "reports on" the cell structure by processes including, but not limited to, binding to the cell structure, either directly or indirectly, and by being incorporated into or contained within the cell structure.

As used herein, the "reference point" is a single point defined relative to the cell structure, including but not limited to a center of the cell structure, a center of mass of the cell structure, a centroid (defined as a geometric center) of the cell structure, or by drawing a bounding box around the cell structure, wherein the point can be defined, for example, as the intersection of any two diagonals within the bounding box. In a preferred embodiment, a centroid of the cell structure is used. Images are acquired of the at least first optically detectable reporter molecule, and the images can optionally be preprocessed (shade corrected and smoothed). The images are then thresholded (preferably using an automatic thresholding procedure), producing a structure mask. In a further preferred embodiment, the cell structure is a nucleus, wherein the structure image is a nuclear image, and wherein the structure mask is a nuclear mask. As used herein, the term "mask" means a processed version of the cell structure image to fill holes. Creation of a mask preferably comprises thresholding the image to select relevant image components with values (position, intensity) above background outside of the structures of interest.

As used herein, the following terms are defined as below:

A cell that is entirely within the FOV is termed an "FOV cell". These are the cells that can be analyzed.

A cell that is entirely outside the FOV is a "Non-FOV cell". These cells are not analyzed.

A Boundary Cell is defined as a cell touching the FOV boundary. Most feature measurements of these cells would be incomplete or inaccurate, and thus Boundary Cells are preferably discounted. However, a Boundary Cell can be considered an intermediate state that can be tracked if desired.

A Departure is defined as a cell leaving, in its entirety, the FOV from any direction. The cell needs to be completely outside the FOV to be called a Departure.

Cells in motion may arrive and depart from the FOV at any time. An Arrival is defined as a cell entering, in its entirety, the FOV from any direction. The cell needs to be completely inside the FOV to be called an Arrival, because until then, it would be an incomplete boundary cell that is generally not analyzed.

Arrivals and Departures add to the complexity of tracking because they require a more complex administration of which cells exist throughout the extent of the entire movie. If all cells exist at all time points, this administration would be a simple array that can be established from analysis of the first time point. If cells are not present at certain time points, it requires an analysis of the full image series to build up this inventory and more elaborate data management.

A Create event is defined as a cell appearing "out of the blue" anywhere in the FOV but not on the edge. For example, a cell may not have had enough labeling intensity to be detected at first, but during the course of the image series it responded and became visible. If a cell appears on the edge, it would be an arrival. A Destroy event is defined as a cell disappearing from the FOV but not moving out as a departure. For example, a cell may die and somehow lose its labeling marker).

There are three general embodiments of the methods and software for tracking individual cells during a kinetic cell screening assay of the invention. Each method provides alternatives to the basic method, each with added sophistication for rejecting fewer cells and providing increased robustness.

1. Simple Proximity Method: In one embodiment, determining a cell identification match comprises identifying reference points in the field of view at a first time point and reference points in the field of view at a second time point that are closest together, and assigning the appropriate cell identification to the cell at the later time point in the image series. This should be successful if most or all of the cells are slow moving (considering the frame rate). Any other data needed to do the comparison at subsequent time points in the image series is stored, including but not limited to the reference points of all the cells from the immediately preceding time point, and the cell ID's which were assigned to each of those cells (ID Mapping Table). In a preferred embodiment, the cell identification match is rejected if it falls below a user-defined threshold for a cell identification match. For example, the user can determine a maximum reasonable distance that cells can move between time point (i.e. a maximum rate of motion), or thresholding can be used to select relevant image components with values (position, intensity) above background outside of the structures of interest.

The successive sets of reference points is preferably matched up as follows. For each cell in the current set, its distance to each reference point in the immediately preceding timepoint is determined. The two closest preceding cells are determined. The closest previous cell is assigned to the current cell, and a quality score (between 0 and 100) is assigned to the match, which increases as the relative distance of the second best match increases. In a preferred embodiment, the quality score is calculated according to the formula:

Quality=100*(SecondBestDistance−BestDistance)/SecondBestDistance

This is preferably used when the distances that the cells moved are small enough so that there is not confusion as to which cell moved where. A quality of match is computed to estimate this. The quality of match is 100% if there is no confusion, and 0% if there is an equal chance that the cell could have been a neighboring cell. In a further preferred embodiment, a cell identification match is rejected if the quality score is below a user-defined threshold for a quality score. The threshold can be defined in various ways, such as those described above, or, given a specific experimental situation for the cells, the user can predict the likelihood of cells being created or destroyed and the acceptable quality score of matching can be set accordingly. For example, the threshold for an acceptable quality of match score can be set be lower if the user is not expecting Create and Destroy events. Cells/artifacts are removed from analysis if they do not map uniquely to a cell ID.

2. Total Distance Minimization: If the Simple Proximity Method results in ambiguous matches (e.g. low quality scores due to two cells equidistant), a global matching may be performed as well. Thus, in a further embodiment, the method further comprises determining a total sum of all distances or distances squared for all possible cell identification matches in successive time points, wherein a smallest total sum of all distances or distances squared is defined as a closest set of cell identification matches.

A matrix of distances between each current and each previous cell is computed. Every possible permutation of the cells, [there are N! permutations]) is scored by summing the distances (or the squares of distances) for all its pairs, with the lowest total being the best cell identification match. In a further preferred embodiment, the amount of computation can be reduced by pre-pairing (using the Simple Proximity Method) any matches with quality scores over a preset threshold, and then excluding the cells in those pre-pairings from the global matching process. This last adjustment will work very well if the cells vary widely in movement rate. Alternatively, the method can reduce the amount of computation by excluding those cells in pre-pairing that fall below a user define threshold from the global matching process.

In a further preferred embodiment, the methods further comprise assigning a quality score to the cell identification match based on a sum of distances or distances squared determined for a second closest cell identification match, and wherein a cell identification match is rejected if the quality score is below a user-defined threshold for a quality score.

3. Total Distance & Feature Matching Minimization: In a further preferred embodiment, defining the cell identification match further comprises comparing other characteristic features of the individual cells between successive time points in order to identify cells, and comparing the measurements for any proposed match. Applied to individual cells, this is a way of efficiently resolving individual ambiguities. As part of a more elaborate method (e.g.: as a follow up to the Total Distance Minimization Method), the feature sets constitute a matrix of better data, which is compared with the vectors for the previous timepoint, and minimizing the weighted sum of differences (or differences squared) as the measure of matching. The matrix would now be better called a confusion matrix, where each position is a compounded number containing the distance+any other cell feature matching values.

Quality of Cell Match

In contrast to the measurement of a quality score based on the simple proximity method, a quality score for the Total Distance & Feature Matching Minimization method is further based on quality of the match based on one or more of any number of cell features, including but not limited to a) actual available features of the cell or subcellular structures, such as fluorescent intensity, cell area, cell shape, etc.; and/or b) additionally created features of the cell such as exogenous tags (i.e.: tags associated with the cells, solely for the purpose of cell tracking), such as "bar-coding tags" (discussed below). The algorithm is designed to work with any set and any number of features, which may change for different assays, cell types, etc.

While the analysis of cell features in determining a quality score can be incorporated into the simple proximity method (e.g.: carried out for possible cell identification matches being analyzed), it is preferred to "pre-pair" cell identification matches via the simple proximity method, and carry out feature analysis only when necessary on those cell identification matches that are ambiguous using the simple proximity method.

Since the cell can change shape and other cell features over time, the quality score is never absolutely perfect. Conversely, different cells may possess similar cell features, and thus can yield a relatively high score for the quality score. Each cell feature may have a different value of contribution to the matching problem. Cell features that have more variation between cells, such as a unique identifier (nuclear texture, intensity, or position with respect to other cell structures such as the perinuclear Golgi apparatus are preferably accorded more weight than those that show less variation between cells such as the position of the whole cell reference point with respect to a nuclear reference point. This preferred embodiment comprises according a weight factor for each cell feature for calculation of the quality score. In one embodiment, a user provides those weight factors. In another embodiment, the weight factor is computed from learning sets and applying a Bayes classifier or other technique.

In a preferred embodiment, the quality score is determined by first calculating its reciprocal, i.e. the difference between cells. This "Mismatch" (preferably weighted) is the sum of the differences between cell features. In a preferred embodiment, the MisMatch between an cell 1 and cell 2 is expressed as follows:

$$\text{MisMatch} = \Sigma\{W_a \cdot DIFF(F_{a1}, F_{a2})\}$$

where

"a" is each cell feature being used $W_a$ is the weight factor for feature a $F_{a1}$ is the feature a computed for cell 1

$DIFF(F_{a1}, F_{a2})$ is the difference function between cell feature a computed for cell 1 and cell feature a computed for cell 2.

The DIFF() function can be defined, for example, as:

$$DIFF(x,y) = ABS(x-y); \text{ (wherein "ABS" means the "absolute number") or}$$

$$DIFF(x,y) = (x-y) \cdot (x-y)$$

The square of the difference helps in making the function "steeper".

For example, one or more of the following cell features can be assessed:

a) Cell size b) Average cell fluorescent intensity c) Cell P2A or shape factor

For these features, the weight factor (Wa, Wb and Wc, respectively) are preferably set to 1.0. For example, the weight of each cell feature can be reduced by using a weighting factor that is a fraction between 0 and 1 while the weight of each cell feature can be increased by using a weighting factor greater than 1. The array of weight factors is given as an input to the algorithm, so it can be easily adapted as needed.

The quality score is simply the reciprocal of the Mis-Match:

$$\text{quality score} = 1/\text{MisMatch}$$

For a "perfect match" the MisMatch is zero, and hence the quality score is infinitely good.

Possible Limitations on the Quality Score

In some instances, the cells may be too "plain" to extract distinctive cell features from them. For example, they may all look like spheres without texture. One way to alleviate this problem is to examine as many unique cell features as possible. For example, multiple fluorescence channels can be analyzed to generate more cell features, for example by labeling multiple structures such as nuclei and Golgi apparatus. Generally, the desirable characteristics of cell features for identifying cells include distinction from neighboring cells and constancy over time.

In a preferred embodiment, a "Bar Coding" scheme is implemented to get even more distinct features added to the cells. Generally, the desirable characteristics of barcoding particles for identifying cells include distinction from each other, from cell-to-cell, and constancy over time. Particles for "bar-coding" cells are available in mixtures of varying intensity, color and size (fluorescent beads of different size and intensity from Bangs Labs, or sets of multispectral Quantum Dots contained within beads, for example), so that most cells can be associated with a particle or set of particles possessing unique features which can thus be uniquely accounted as unique cell features. Bar code particles can be contained within cells by random distribution to cells and natural phagocytosis of the particles. Alternate methods can be employed to increase the yield of labeled particles and the uniformity of labeling, including physical projection or injection of particles, or by depositing cells onto ordered arrays of barcode particles deposited on substrates to control the number and distribution of particles delivered to cells. Barcode particles need not be associated on a perfect one-to-one basis with cells to provide value for cell identification. The methods described here are fault tolerant and imperfect bar coding contributes to cell identification even if barcodes are not contained within every cell or if barcodes are repeated occasionally within the image. Barcode particles can be observationally associated with cells by, for example, their proximity to a labeled nuclei or other cell structure or by being contained within the cell periphery. In these instances, the "bar code" features are treated just like any other cell feature in the quality score equation above. In favorable instances, distribution, uniqueness and universality of the bar coding particles is sufficient and no supportive biological structures are required to associate particles with unique cells. If the bar coding technique is very high quality with a majority of cell containing a unique barcode, the weight factor for the bar code cell feature can be very high, completely supplanting the need to label endogenous cell structures. A less stringent bar coding scheme is given a lower weight factor and simply contributes a part in the process of matching.

In other instances, the cells may change their shape and cell features so much when imaged from timepoint to timepoint that their identification at different time points as the same cell is difficult. This problem is alleviated by sampling often enough in time (increased Sampling Frequency), to ensure the variability over time is less than the variability between cells.

The Sampling Frequency means the number of image acquisitions per minute. An insufficient sampling frequency reduces the ability to effectively track cells, or measure fast cellular events. An excessive sampling frequency may damage the cells due to phototoxicity. An optimal sampling frequency will thus vary depending on various factors, including cell motion, cell density, the cellular event being analyzed, and the probabilities of arrivals (move into FOV), departures (leave FOV), and collisions with other cells. For example high speed calcium changes may require a faster sampling frequency to satisfy the tracking needs than most assays. In general, an optimal sampling frequency is the minimum frequency needed to be able to reconstruct a signal with arbitrary precision (ie: the Nyquist sampling frequency). One way to find this frequency is to look at the Fourier spectrum of the original signal and find the highest frequency component. The Nyquist sampling frequency is twice that frequency. Sampling below the Nyquist frequency may not allow reconstruction of the higher frequency components of the signal and, may produce aliasing artifacts.

It is also desirable to optimize the "Yield" of the kinetic assay. The yield can be expressed as an absolute number of cells that maintain a Free Path (i.e.: no collisions), or as the percentage of those cells compared to the total cells. The probability of a Free Path is the likelihood of a cell not being involved in any collisions, and not leaving or entering the FOV during the entire image acquisition. This probability will go down the longer kinetic data is acquired, since sufficient cell motion can eventually cause all cells to collide or move from the FOV, and is dependent on the cell motion and the cell density.

Given a particular cell density (e.g.: number of cells per square area), a user can compute average distance between cells. If a FOV has an extremely high cell density, it will have the potential for a high yield, but probably all cells will be colliding within the first few image acquisitions, reducing the yield to zero. Hence, it is useful to determine an optimal cell density to produce an optimal yield, for a given set of cell behavior parameters. The optimal cell density will vary based on all of the various factors discussed herein, and thus is preferably determined experimentally or by computer simulation. For example, the optimal experimental cell density will depend on the biological function of cells to be measured and on the statistical error desired for measurement of the sample.

An optimal cell density, accounting for biological variables, is between 10 and 50% of confluency.

The average distance between cells may need to be corrected for cell confluency (e.g.: percentage of cells that are touching other cells) or cell clustering. Given an average cell motion speed estimate, we can set the maximum sampling frequency allowed to satisfy the "Nyquist" criterion. The cell motion speed is preferably expressed as an average distance traveled per time point of the image acquisition. Cell motion can also be described by defining its speed and persistence in a direction (Directed motion), by a diffusion coefficient (Brownian motion), and/or by defining an affinity factor, which reflects the effect of nearby cells on the motion of a cell.

Rolling Average of the Quality Score

The quality score can be averaged over multiple time points and applied to a later time point as an average quality score. This "rolling average" will become part of the feature vector computed for each cell at each timepoint. This way, it is carried forward during the analysis of each image acquisition, without the need to access the entire image acquisition series.

In a preferred embodiment, at time point t, this is defined as:

Average quality score$_t$=(1−k)·Average quality score$_{(t−1)}$+k·quality score$_t$ where k is constant to define the weight factor of this geometric average. The value of k can be determined experimentally by providing the best fit with sample truth data where cell identification is pre-determined. The choice of k depends on the sampling frequency relative to the amount of change in the cells, and on the desired amount of smoothing of the feature over time. A value of k close to 1 will do little or no smoothing, while a value close to zero will do a lot of smoothing. The average quality score value is set it with a value that reflects expectation at the beginning of the image acquisition series. The method does not require control or truth data but the parameters used to calibrate the method for a specific biological sample are preferably derived experimentally from control data that matches the experimental sample in the measures used for cell identification. For example, control experiments can be run, or a reasonable expectation for that value can be provided.

4. Reduction of the Confusion Matrix: The computational cost of the Total Distance & Feature Matching Minimization method and a complete confusion matrix can be quite high, and grows rapidly with the number of cells. Therefore, in a preferred embodiment, the computationally less intensive Simple Proximity method is used first, and only those cell identification matches that are ambiguous are subjected to confusion matrix analysis, as necessary.

The strategy looks as follows:

a) Try to match cells based on Simple Proximity b) Identify problem areas where Simple Proximity may not work c) Compute confusion matrices for those areas—on a limited set of cells d) Solve confusion matrices for the problem areas

EXAMPLES

Determining When the Simple Proximity Method is Insufficient

As described in the previous version, we can consider two examples. Then we proceed with the strategy to assign the right method to the job.

1. Very Simple Case

Three cells (a, b and c), each one moves a bit to the right and they will become A,B and C in the next time point:

a A
b B
c C

// Program output . . .
Test 1 . . . 3 cells move to the right
Previous Image:

| Label | Xcm | Ycm | CellID |
|---|---|---|---|
| 0 | 100 | 100 | 1 |
| 1 | 200 | 200 | 2 |
| 2 | 300 | 300 | 3 |

New Image:

| Label | Xcm | Ycm | CellID | Quality | New? | dY | dX | Distance |
|---|---|---|---|---|---|---|---|---|
| 0 | 120 | 100 | 1 | 100% | Old | 20 | 0 | 20.00 |
| 1 | 225 | 200 | 2 | 100% | Old | 25 | 0 | 25.00 |
| 2 | 330 | 300 | 3 | 100% | Old | 30 | 0 | 30.00 |

Distance matrix:

| | 0 | 1 | 2 |
|---|---|---|---|
| 0 | 20.00 | 128.06 | 269.07 |
| 1 | 160.08 | 25.00 | 125.00 |
| 2 | 304.80 | 164.01 | 30.00 |

2. The More Difficult Case

Three cells, each one moves a bit to the right. This sounds the same as #1, but now the proximity of the new locations makes the situation confusing:

| a | A b | | B |
|---|-----|---|---|
| | | c C | |

This situation is almost the same as the simple example, but forms a major tracking problem. For example: A and C are closer to b than to a or c. Using the simple proximity method, the following results are obtained:

a is lost, b moved to A or C, B is a "new cell" and c moved to A

This situation requires the more complex proximity matrix and competitive matching portion of the algorithm to come up with a best global fit for all cells involved. The algorithm can track this, by using the Distance Minimization function of the algorithm. (See below)

// Program output . . .
Test 4 . . . 3 cells move to the right, but are too close for simple matching
Previous Image:

| Label | Xcm | Ycm | CellID |
|-------|-----|-----|--------|
| 0 | 100 | 100 | 1 |
| 1 | 125 | 100 | 2 |
| 2 | 105 | 105 | 3 |

Simple proximity method:
New Image:

| Label | Xcm | Ycm | CellID | Quality | New? | dX | dY | Distance |
|-------|-----|-----|--------|---------|------|-----|-----|----------|
| 0 | 120 | 100 | 2 | 100% | Old | −5 | 0 | 5.00 |
| 1 | 145 | 100 | 3 | 12% | Old | 40 | −5 | 40.00 |
| 2 | 125 | 105 | 1 | 100% | Old | 2 | 5 | 25.00 |

Simple proximity method failed
Now look at the distance matrix more closely:
Distance matrix:

| | 0 | 1 | 2 |
|---|---|---|---|
| 0 | 20.00 | 5.00 | 15.81 |
| 1 | 45.00 | 20.00 | 40.31 |
| 2 | 25.50 | 5.00 | 20.00 |

| matching permutation | computed total distance weight |
|----------------------|-------------------------------|
| 0 1 2 | |
| \| \| \| | |
| 0 1 2 | 20.00 + 20.00 + 20.00 = 60.0 |
| 0 2 1 | 20.00 + 5.00 + 40.31 = 65.31 |
| 1 0 2 | 45.00 + 5.00 + 20.00 = 75.0 |
| 1 2 0 | 45.00 + 5.00 + 15.81 = 65.81 |
| 2 1 0 | 25.50 + 20.00 + 15.81 = 61.31 |
| 2 0 1 | 25.50 + 5.00 + 40.31 = 75.81 |

Hence 0 1 2 is the best matching sequence
Total Distance Minimization method:
New Image:

| Xcm | Ycm | CellID | Quality | New? | dX | dY | Distance |
|-----|-----|--------|---------|------|-----|-----|----------|
| 0 120 | 100 | 0 | 100% | Old | 20 | 0 | 20.00 |
| 1 145 | 100 | 1 | 12% | Old | 20 | 0 | 20.00 |
| 2 125 | 105 | 2 | 100% | Old | 20 | 0 | 20.00 |

So How Do We Know We Could Be Dealing with an Example 2 Instead of 1?

If there are lots of close contenders in the area, one could simply assume the simple proximity method will run in to its limitations.

Secondly, Create and Destroy events suggest the existence of an "aliasing" effect. It may be difficult to distinguish Create and Arrival events if the sampling frequency is too low to make a proper judgment. At a low sampling frequency, a cell that suddenly appears near the boundary could have been a creation, or could simply have moved in quickly as an arrival. The same applies for Destroy and Departure events. Note that an Arrival may also occur if a cell enters the FOV "from above". This means a cell is floating higher than the depth of field and lands in the FOV. Most observed Create and Destroy events are caused by artifacts, such as a focus or signal-to-noise problem. If the problem is corrected in a subsequent time point, the same cell will show up as a Create event.

For example:

a Ab B

The simple conclusion would be:

a is destroyed, b moves to A, and B is new creation.

In addition to the Create and Destroy clues, one can use an Aver LastMoveDist value to define a "sphere of influence".

Last Distance Moved

To assess the amount of movement expected from an individual cell, the distance moved from the previous time point can be recorded. Although past performance is not a true indication of how much the cell may move now, it is better than no indication at all.

In a preferred embodiment, at time point t, this is defined as:

$$\text{LastMoveDist}_t = SQRT((posx_{(t-2)} - posx_{(t-1)})^2 + (posy_{(t-2)} - posy_{(t-1)})^2)$$

This value needs to be set it with a value that reflects expectation at the beginning of the image acquisition set. For example, control experiments can be run, or a reasonable expectation for that value can be provided.

Rolling Average of Last Distance Moved

Since the motion of a cell can seem erratic, it is preferred to average a few time points rather than using a single time point. Thus, a further preferred embodiment comprises carrying forward a rolling average of distance moved to each new time point.

In a preferred embodiment, at time point t, this is defined as:

$$\text{Average LastMoveDist}_t = (1-k) \cdot \text{LastMoveDist}_{(t-1)} + k \cdot \text{LastMoveDist}_t$$

Where k is constant to define the weight factor of this geometric average. The choice of k depends on the sampling frequency relative to the amount of change in the cells, and on the desired amount of smoothing of the feature over time. A value of k close to 1 will do little or no smoothing, while a value close to zero will do a lot of smoothing. The Average LastMoveDist value needs to be set with a value that reflects expectation at the beginning of the image acquisition set. For example, control experiments can be run, or a reasonable expectation for that value can be provided.

In a preferred embodiment, identifying cells or groups of cells that require analysis by the confusion matrix comprises:

1. Find the largest Average LastMoveDist of all cells in this field. This is a good indication of the motility of these cells. This number can be multiplied by a safety factor, for example by 1.3, to allow for e.g. 30% more motility than was previously seen. The only cost of increasing this number is computation time.
2. For each cell, compute a sphere of influence using this inflated Average LastMoveDist number. The purpose is to generate a large enough sphere, to assure not generating false Create and Destroy Events. However, the sphere is small enough (i.e.: preferably 10 cells or less) so that the confusion matrix of all cells inside the sphere of influence does not become so large that it becomes too computationally intensive.

3. Merge spheres by propagation if they overlap. For example, when two spatially distinct clusters of cells share only one cell that is close enough be part of either cluster, those clusters need to be merged into one.

4. The spheres result in groups of cells that "may have something to do with each other." They are not really spheres anymore by that time, just a list of cell ID's. Any time that there is more than one contender in a sphere, it can be assumed that the simple proximity method is inadequate, and the more complex matching methods are utilized.

Confusion Matrix

If the previous step identifies the need for complex matching, a confusion matrix can be computed. In one embodiment, the confusion matrix is conducted on small groups of cells, preferably less than twenty cells, and even more preferably fifteen cells or fewer.

For example, if there are three cells in the group, a vector such as the one below is created:

$$\begin{array}{ccc} MM_{1,1} & MM_{1,2} & MM_{1,3} \\ MM_{2,1} & MM_{2,2} & MM_{2,3} \\ MM_{3,1} & MM_{3,2} & MM_{3,3} \end{array}$$

where $MM_{1,2}$ is the MisMatch of Cell 1 compared with Cell 2, etc. The computed distance between the cells can be added to the MM matrix elements at this point and use it in the same computation as another matching feature.

Real Arrival/Departure and Create/Destroy Events

Using the above matrix will always generate a match, even if there are Arrival/Departure and create /destroy events.

It is preferred that there be a limit at which a match is rejected, and at that point a create and/ or a destroy event is present. The average quality score can be used for this purpose. This figure can be multiplied by an allowance factor to come up with a threshold value. The "allowance factor" is preferably arrive at by balancing the likelihood of a Create/Destroy event with the performance of the tracking precision. The threshold can also be set externally, if enough learning data sets of specific cell types and assays have been generated by which to establish an appropriate threshold.

Reduction of the Confusion Matrix

The confusion matrix can become very hard to solve if the number of cells in a confusion cluster is larger than about 10–20 cells. The number of permutations that need to be evaluated is proportional to the factorial of the number of cells in the cluster. This can be avoided by setting the maximum reasonable distance between cells low enough, and using a sampling frequency that is appropriate, based on previous test data and setting new standards for the preparation and assay parameters. Use of this "matrix reduction method" allows handling of larger confusion matrices of, for example, 20–40 cells, at a fraction of the computational time.

Alternatively, the efficiency of solving the confusion matrix can be increased by using the distance matrix to "pre-screen" the confusion matrix elements. This method involves excluding any cell identification matches with a quality score at or above a user-defined threshold for quality scores (as determined by the distance matrix), from the confusion matrix.

The cell tracking methods disclosed herein provide information on the continuity of cell identification from time point to time point in a kinetic cell screening assay. To integrate the information with a cell screening assay(s), the results from the cell tracking methods are preferably managed so that cell and well features, and kinetic output features, can be associated with the correct cells, Relating assay output features to cell identification requires additional data management. Optimal computation of kinetic features (cell-based or well-based) depends on a cell data management algorithm (FIG. 1) that works in conjunction with the cell tracking module. The data management serves three important purposes: (1) to dynamically relate the list of output features and cell ID's to each other; (2) to enable modification of the assay output data by the results of cell tracking; (3) to enable the correct sorting of data sets obtained from multiple images. For example, assay data may be eliminated for invalid cells. Cells may be marked as invalid if for example they are present at some time points but not other time points.

At each time point the cell data need to be rearranged in accordance with current cell ID (kinetics cell ID) so that cell kinetic data can be computed. Then, the kinetic data need to be realigned with cell ID's again for well statistics to be computed. Statistics can be done on all cells in a well or only on fully tracked cells, depending on the needs of the user. The data management algorithm keeps track of all newly identified cells (at any current time point), thus, allowing the user to identify the time interval (starting time point and ending time point) during which each cell has been tracked. This, in its turn, makes it possible to flag cells that were fully tracked from the beginning of the experiment to the end of it. The ability to select cells that fit certain cell ID criteria is valuable for producing optimal kinetic data on the cell level. While population averaged data may be minimally affected by the loss or gain of a few cells, the cell level kinetic data can be dramatically affected by mis-identification or by cells that are not detectable throughout the entire experiment. In another aspect, the present invention comprises computer readable storage medium comprising a program containing a set of instructions for causing a cell screening system to execute procedures for tracking individual cells during a kinetic cell screening assay, wherein the procedures comprise the various method steps of the invention. The computer readable medium includes but is not limited to magnetic disks, optical disks, organic memory, and any other volatile (e.g., Random Access Memory ("RAM")) or non-volatile (e.g., Read-Only Memory ("ROM")) mass storage system readable by the CPU. The computer readable medium includes cooperating or interconnected computer readable medium, which exist exclusively on the processing system or be distributed among multiple interconnected processing systems that may be local or remote to the processing system.

In a preferred embodiment, the cell screening system comprises a fluorescence optical system with a stage adapted for holding cells and a means for moving the stage, a digital camera, a light source for receiving and processing the digital data from the digital camera, and a computer means for receiving and processing the digital data from the digital camera. This aspect of the invention comprises programs that instruct the cell screening system to define the organization of the cellular component(s) of interest in individual cells, using the methods disclosed herein.

The methods of the invention can be used in conjunction with any cell-based screening assay, including multiparametric assays, that can benefit from kinetic analysis. A series of biologically important metabolites, regulatory molecules, and organelles (such as those shown in Table I), can be labeled with fluorophores and activity or concentrations determined by measuring intensity changes over time. A majority of these indicators require intact, living cells which inherently change over time. Therefore, single cell kinetic intensity measurements are required for high content information from these indicators. Most of the small molecule indicators listed in Table I (including trademarked indicators) are available from Molecular Probes.

making DNA constructs of the protein of interest that contains additional code for a Green Fluorescent Protein (GFP). These bioreporters are expressed in cells to produce functional protein that is fluorescently labeled. These probes would be useful as i) a target validation tool with which the levels of potential therapeutic targets expressed in genetically engineered cells could be monitored, or ii) a screening tool with which the effects of compounds on levels of GFP—[Promoter of Interest] fusion proteins could be monitored. The time of response is on the order of hours to days.

TABLE 1

Intensity Based Indicators of Biomolecular Activity

| Target | Fluorescent Indicator |
| --- | --- |
| $Ca^{2+}$ | Fluo4, FLIPR, Indo1, Fura-2 |
| $Mg^{2+}$ | Mg-Fura-2 |
| $Na^+$ | SBFI |
| $K^+$ | PBFI |
| $Cl^-$ | SPQ |
| Metal Ions: | Calcein, Calcium Green-1, BTC-5N, |
| $Zn^{2+}$, $Cu^+$, $Cu^{2+}$, $Cd^{2+}$.$Hg^{2+}$, $Ni^+$, $Co^{2+}$, $Pb^{2+}$, $Fe^{2+}$, $Fe^{3+}$, $Ba^{2+}$, $As^{3+}$, $Tb^{3+}$, $La^{2+}$ | FITC_Gly, -His, TCCP, TSPP, APTRA-BTC |
| pH | BCECF, SNARF, SNAFL, NERF |
| Gene Expression | GFP-cDNA chimera with gene of choice |
| Proliferation and DNA content | Hoecsht, DAPI |
| Viability | Live/Dead dyes such as CMFDA or Calcein (live)/Propidium Iodide (dead) |
| Membrane Potential | DiBAC |
| Cellular organelles | MITOTRACKER ™, JC-1,, LYSOTRACKER ™, Fluorescein-Dextran, Carbocyanin and ceramide dyes |
| Nitric Oxide/Reactive Oxygen Species | Chloro-Fluorescein |
| Phosphoinositides | Bodipy-Inositol |
| Cyclic AMP | PKA Chimeras and covalently labeled proteins |
| Multi Drug Resistance transporter | Doxorubicin, Rhodamine –123 |
| Protease activity | Amino-coumarin substrate peptides |
| Cell Surface and Intracellular Receptors | Various Fluorescent Ligands |

Ligand Binding

Ligands for cell surface receptors bind specific extracellular ligands. Some native ligands induce molecular function while other exogenous molecules such as drugs bind, partition in subcellular compartments and modulate biomolecule function. Ligands that are fluorescently labeled can be monitored for binding to the cell. Fluorescent EGF binding to Epidermal Growth Factor Receptor occurs within a few minutes, activating the receptor. After surface binding, the EGF—receptor complex internalizes into endosomal compartments, indicating down-regulation and termination of the signal. Binding and internalization can be detected using the kinetic methods of the invention.

Cell Viability

Intact plasma membranes can be detected by introducing indicators that pass through intact cell membranes and are trapped intracellularly by enzymatic removal of side groups needed for membrane permeability. Dyes remain trapped, labeling cells, unless the plasma membrane is ruptured, releasing the internalized dyes. Acetoxymethyl ester derivatives of calcein work well as indicators of intact cell membranes and viable cells. Ongoing viability of the cells can be monitored in conjunction with the kinetic methods of the invention.

GFP Expression

The kinetic methods of the invention can be used to monitor expression of proteins over time. Many proteins can be fluorescently labeled without perturbing function by Nitric Oxide/Reactive Oxygen Species Nitric Oxide is an important signaling molecules in neuron and endothelial cells and controls vascular tone, and cell communication. This application could be used as a screening tool, or as a cytotoxicity tool to monitor production of reactive oxygen species. These molecules are important pharmacological targets for stroke, Alzheimer's disease, Parkinson's disease and congestive heart failure. The time of response is on the order of 1–10 minutes, and thus could be developed using the kinetic methods of the invention.

Multiple Drug Resistance (MDR)

This application can be used to monitor the activity of the cell surface transporter, P-glycoprotein. This is a molecular pump that is embedded in plasma membrane and pumps anticancer drugs out of cells, rendering the cells resistant to a wide variety of therapeutic agents. The time response for this assay is on the order of minutes, and thus could be developed using the kinetic methods of the invention. This assay would be applicable to anticancer therapies.

Lysosome pH

Fluorescein labeled dextrans are taken up into the cell by endocytosis and end up in lysosomal compartments where the dextrans are degraded. The intensity of fluorescein is pH dependent and so measuring intensity over time is sufficient to detect changes in lysosomal activity induced by drugs such as the proton ionophore, monensin.

In a preferred embodiment of the use of the kinetic methods of the invention in conjunction with a cell screening assay, cells are segmented by contacting the cells with a nuclear label and using information from the nuclear channel. Images from the nuclear channel can optionally be preprocessed (shade corrected and smoothed) and are thresholded (using an automatic thresholding procedure), producing a nuclear mask. By drawing lines equidistant to nuclei edges (water shed approach) the nuclear zones of influence (non touching cellular domain masks) are identified and the mask of the domains is created. For each nuclear mask, an extended nuclear mask is created (nucleus mask is dilated a number of times that is dependent upon the cell type and size). The logical "AND" of the mask with corresponding cellular domain results in a final mask that is then applied to the second channel to measure the fluorescence intensity of the relevant fluorescent marker under the mask. Nuclei are masked and cells are segmented by defining domains outside of each nuclei with a watershed routine. Kinetic features are then determined, based on the changes in intensity in individual cells from one measurement to the next, as described above.

By determining the intensity of the fluorescence emitted by the markers in individual cells at various time points, the method provides cell-based, kinetic measurements of one or more of the following:

Dynamic changes in intensity over time

Heterogeneity of intensity among cells

Repetitive oscillations in intensity

Waves of intensity changes through connected cells

Subpopulations of responding cells

Sequential activation of signaling molecules

In a preferred embodiment, the method provides a quantal response of cells (i.e.: percent of responding cells with an intensity above a threshold value), which increases the value of the present assay over those assays that measure only the raw amplitude of response. The threshold to be used for a particular parameter can be determined for each time point, and the value(s) of the thresholds can be set before the scan as an assay input parameter, or can be reset during data analysis.

In a further preferred embodiment of the invention, the kinetic measurement is modified, sorted, and/or excluded depending on the quality score for the cell identification match for each cell. Sorting includes pooling data for all cells of some group, such as fast cells, cells on the 5th image set, cells with red markers, and subpopulations of large cells.

In the case of calcium assays, kinetic features that can be determined include, but are not limited to:

Cell-based Kinetic Features:

Intensity—Cell averaged fluorescent intensity averaged over time

Prestim Intensity—the baseline intensity value prior to stimulation by agonist (averaged value over all prestim points)

Peak Intensity—Peak intensity value (Highest point or curve fit to find inflection point)

Relative Peak Intensity Value—Peak Intensity/Prestim Intensity.

Time to Peak Intensity

Plateau Intensity

Relative Plateau Intensity

Integrated Intensity of Ca2+Signaling

Oscillation frequency

Oscillation persistence

Oscillation amplitude

Well-based Kinetic Features:

Avg Fluorescent Intensity

Avg Baseline Intensity

Avg Peak Intensity

Avg Relative Peak Intensity

Avg Time to Peak Intensity

Avg Plateau Intensity to plateau and asymptote

Avg Relative Plateau Intensity

Avg Integrated Intensity of Ca2+Signaling

Avg Oscillation Frequency

Avg Oscillation Persistence

Avg Oscillation Amplitude

What is claimed is:

1. A method for tracking individual cells during a kinetic cell screening assay, comprising:

a) providing cells that possess at least a first luminescently labeled reporter molecule that reports on a cell structure;

b) obtaining a structure image from luminescent signals from the at least first luminescently labeled reporter molecule in the cells in a field of view at a first time point;

c) creating a structure mask from the structure image obtained at the first time point for individual cells in the field of view;

d) defining a reference point relative to each structure mask;

e) assigning a cell identification to each reference point in the field of view;

f) obtaining a structure image from luminescent signals from the at least first luminescently labeled reporter molecule in the cells in the field of view at a later time point and creating a structure mask from the structure image obtained at the later time point for individual cells in the field of view;

g) repeating steps (d)–(e) at the later time point;

h) correlating cell identification between the first time point and the later time point by calculating a distance between reference points in the field of view at the first time point and reference points in the field of view at the later time point; and i) defining a cell identification match by identifying reference points in the field of view at the first time point and reference points in the field of view at the later time point that are closest together, thereby tracking individual cells.

2. The method of claim 1, further comprising repeating steps (f)–(i) a desired number of times, wherein determining the distance between reference points is done by determining a distance between reference points in successive time points, and wherein defining the closest cell identification match is done by defining the closest cell identification match in successive time points.

3. The method of claim 1 wherein a cell identification match is rejected if the cells identified as a cell identification match are farther apart than a user-defined limit.

4. The method of claim 3 further comprising assigning a quality score to the cell identification match based on a distance determined for a second closest cell identification match, and wherein a cell identification match is rejected if the quality score is below a user-defined threshold for a quality score.

5. The method of claim 4 wherein the quality score is calculated by a method comprising dividing the difference between the distance between reference points in the closest cell identification match from the distance between reference points in the second closest cell identification match by the distance between reference points in the second closest cell identification match.

6. The method of claim 4 wherein the quality score is averaged over multiple time points and applied to a later time point as an average quality score.

7. The method of claim 1 further comprising determining a total sum of all distances or distances squared for all possible cell identification matches in successive time points, wherein a smallest total sum of all distances or distances squared is defined as a closest set of cell identification matches.

8. The method of claim 7 further comprising assigning a quality score to the cell identification match based on a sum of distances or distances squared determined for a second closest cell identification match, and wherein a cell identification match is rejected if the quality score is below a user-defined threshold for a quality score.

9. The method of claim 8 further comprising determining a distance moved by the individual cell in successive time points.

10. The method of claim 9 further comprising determining an average distance moved by an individual cell over multiple time points.

11. The method of claim 8 further comprising excluding from the determining a total sum of all distances or distances squared for all possible cell identification matches in successive time points any cell identification matches with a quality score at or above a user-defined threshold for quality scores.

12. The method of claim 11 wherein defining the cell identification match further comprises comparing other features of the individual cells between successive time points.

13. The method of claim 12 wherein the features comprise one or more features selected from the group consisting of area, shape, size, and luminescent intensity of cell or subcellular structures, and exogenous tags associated with cell or subcellular structures.

14. The method of claim 13 wherein the feature comprises an exogenous tag, and wherein the exogenous tag comprises a bar coding tag.

15. The method of claim 13 further comprising excluding any cell identification matches with a quality score at or above a user-defined threshold for quality scores from the comparing other characteristic features of the individual cells between successive time points.

16. The method of claim 13 further comprising excluding any cell identification matches with a quality score below a user-defined threshold for quality scores from the comparing other characteristic features of the individual cells between successive time points.

17. The method of claim 1 wherein the cell structure is a nucleus, wherein the structure image is a nuclear image, and wherein the structure mask is a nuclear mask.

18. The method of claim 1, wherein the cell screening assay comprises one or more assays for the kinetic analysis of a cell parameter selected from the group consisting of ionic concentration, pH, gene expression, DNA proliferation, DNA content, cell viability, membrane potential, production of reactive oxygen species, enzyme activity, receptor activation, ligand binding, and transporter activity.

19. The method of claim 18, wherein the cells further possess at least a second luminescently labeled reporter molecule that reports on the cell parameter, and wherein the method further comprises obtaining luminescent signals from the second luminescently labeled reporter molecule and calculating a kinetic measure of the luminescent signals from the second luminescently labeled reporter molecule in individual cells, wherein the kinetic measure is selected from the group consisting of dynamic changes in intensity over time, heterogeneity of intensity among cells, oscillations in intensity, waves of intensity changes through connected cells, subpopulations of responding cells, and sequential activation of signaling molecules.

20. The method of claim 19, wherein the kinetic measure is modified, sorted, and/or excluded depending on a quality score for the cell identification match for each cell.

21. A computer readable storage medium comprising a program containing a set of instructions for causing a cell screening system to execute procedures for tracking individual cells during a kinetic cell screening assay, wherein the procedures comprise a) obtaining a structure image from luminescent signals from at least a first luminescently labeled reporter molecule in cells in a field of view at a first time point;

b) creating a structure mask from the structure image obtained at the first time point for individual cells in the field of view;

c) defining a reference point relative to each structure mask;

d) assigning a cell identification to each reference point in the field of view;

e) obtaining a structure image from luminescent signals from the at least first luminescently labeled reporter molecule in the cells in the field of view at a later time point and creating a structure mask from the structure image obtained at the later time point for individual cells in the field of view;

f) repeating steps (c)–(d) at the later time point;

g) correlating cell identification between the first time point and the later time point by calculating a distance between reference points in the field of view at the first time point and reference points in the field of view at the later time point; and h) defining a cell identification match by identifying reference points in the field of view at the first time point and reference points in the field of view at the later time point that are closest together, thereby tracking individual cells.

* * * * *